United States Patent [19]

Fundock

[11] Patent Number: 5,470,325
[45] Date of Patent: Nov. 28, 1995

[54] OSTOMY BAG WITH COMBINATION VENTING/CLEANING ASSEMBLY

[76] Inventor: Michael Fundock, R.D. #3, Box 256, Benton, Pa. 17814

[21] Appl. No.: 843,259

[22] Filed: Feb. 28, 1992

[51] Int. Cl.⁶ ..................................................... A61F 5/44
[52] U.S. Cl. ............................................ 604/332; 604/334
[58] Field of Search .................... 604/327, 332, 604/333, 334, 336, 335, 339, 340, 277, 337, 338, 341, 342, 322, 353; 56/202

[56] References Cited

U.S. PATENT DOCUMENTS

| | | | |
|---|---|---|---|
| 2,496,175 | 1/1950 | Perry | 604/335 |
| 2,504,872 | 4/1950 | Perry | 604/334 |
| 2,540,777 | 2/1951 | Deahl | 604/334 |
| 2,800,905 | 7/1957 | Simmons et al. | 604/333 X |
| 3,690,320 | 9/1972 | Riely | 604/333 |
| 4,149,363 | 4/1979 | Woelffer et al. | 56/202 |
| 4,403,991 | 9/1983 | Hill | 604/341 X |
| 4,465,486 | 8/1984 | Hill | 604/341 X |
| 4,561,858 | 12/1985 | Allen, Jr. et al. | 604/332 X |
| 4,586,927 | 5/1986 | Jensen | 604/334 X |
| 4,863,447 | 9/1989 | Smith | 604/324 X |
| 5,022,693 | 6/1991 | Loveless | 604/332 X |
| 5,037,408 | 8/1991 | Henry | 604/334 X |

FOREIGN PATENT DOCUMENTS 8701932  4/1987  WIPO ...................... 604/333

Primary Examiner—Mary Beth O. Jones
Attorney, Agent, or Firm—Aquilino & Welsh

[57] ABSTRACT

An ostomy bag including a combination venting\cleaning assembly which allows gases to be exhausted from the bag through a first opening in a closure wherein the closure is removable so as to provide a larger opening for cleaning or flushing purposes. The bag further includes a handle attached to the tailpiece, which may be grasped by the user during the cleaning process in order to avoid contact with the bodily waste products collected within the bag.

17 Claims, 2 Drawing Sheets

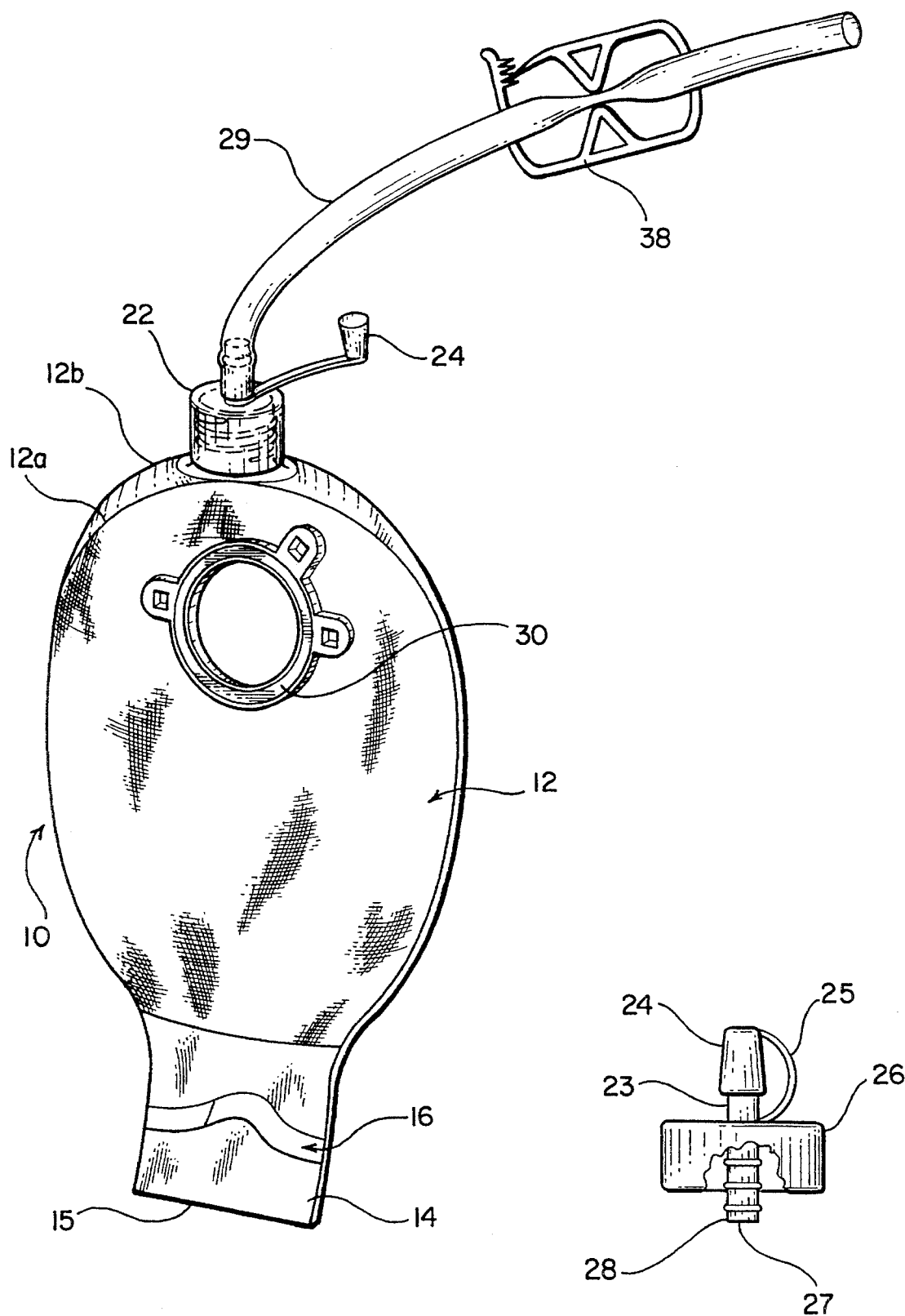

OSTOMY BAG WITH COMBINATION VENTING/CLEANING ASSEMBLY

BACKGROUND OF THE INVENTION

1. Field of the Invention

The present invention is directed to an ostomy bag. More particularly, the present invention provides improvements to an ostomy bag which are intended to aid a patient in handling an ostomy bag during cleansing so that the bag may be reused while at the same time incorporating a venting system. The ostomy bag of the present invention is incorporated with a venting/cleaning assembly which allows gases built up within the ostomy bag during use to be vented in a first mode, and allows cleaning of the ostomy bag while secured to a patient or when removed from a patient in a second mode.

2. Description of the Prior Art

Over millions of patients have undergone a surgical procedure referred to as an ostomy. This is where a portion of the colon or other body member is surgically attached to an opening formed in the abdominal wall. This opening forms a stoma, which does not have a sphincter muscle, thus requiring some form of bag to be worn over the stoma to collect bodily discharges and to retain them until the bag can be removed and cleaned or replaced in the privacy of one's own home. To dispose of each ostomy bag after every use would become quite expensive, and therefore ostomy bags which may be cleaned and then reused have been developed. A problem associated with cleaning the bag is that no one wants to come into contact with bodily waste products, and thus handling of the bag requires some manual dexterity skills which the elderly at times find difficult.

Another problem associated with an ostomy bag is that gases accumulate within the bag while it is being worn. The gases need to be vented, otherwise the bag will expand and unseal itself, creating an embarrassing mess.

There are prior art devices, such as in Smith U.S. Pat. No. 4,863,447 and Diack U.S. Pat. No. 2,054,535, which have incorporated a venting system into an ostomy bag and there are prior art devices which hold the bag during cleaning, note the patent to Loveless U.S. Pat. No. 5,022,693. However, there are no prior art devices known which address both the problems of venting and cleaning by incorporating improvements into the ostomy bag itself.

SUMMARY OF THE INVENTION

The present invention is an ostomy bag with a tailpiece terminating in a discharge opening at one end, a combination venting/cleaning assembly located at its other end, and a mouth rim means positioned between the ends of said bag. The venting/cleaning assembly includes a tubular extension piece having a portion which is connected to or formed with the bag, which is sufficiently rigid in order to maintain the upper sides of the bag spaced apart and an outer portion which extends outside of the bag and is either externally or internally threaded. The outer threaded portion of the extension piece serves as a cleaning or flushing opening in a first mode of operation, and as a vent opening in a second mode of operation. In the second mode, the extension piece is closed with a threaded closure having a vent hose coupling thereon. The vent hose coupling having a bore therethrough which functions as a vent. In the first mode, the closure is removed, providing a larger size opening through which liquids can be flushed. The device further includes a flexible handle on the tailpiece, making the tailpiece easier to manipulate.

It is an object of the present invention to provide an ostomy bag which is versatile and easy to manipulate by elderly patients.

Another object of the invention is to provide an ostomy bag which is easy to handle and clean when removed.

A further object of the present invention is to provide an ostomy bag which can be cleaned while being worn.

Still another object of the invention is to provide an ostomy bag including a venting system to control the escape of gases which build up within the bag during use.

Yet a further object of the invention is to provide a combination venting/cleaning assembly located above the mouth rim means on the ostomy bag, thereby preventing clogging of the venting system and allowing easy cleaning of the bag from top to bottom.

A further object of the invention is to provide an ostomy bag with a handle on the tailpiece in order to prevent a patient from coming in contact with the bodily waste collected within the ostomy bag when being discharged.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a perspective view of the invention in a second venting mode of operation wherein the threaded closure is attached thereto in combination with a hose and pinch clamp.

FIG. 3 is a detailed view of the threaded closure.

DESCRIPTION OF THE PREFERRED EMBODIMENTS

Figure 1:
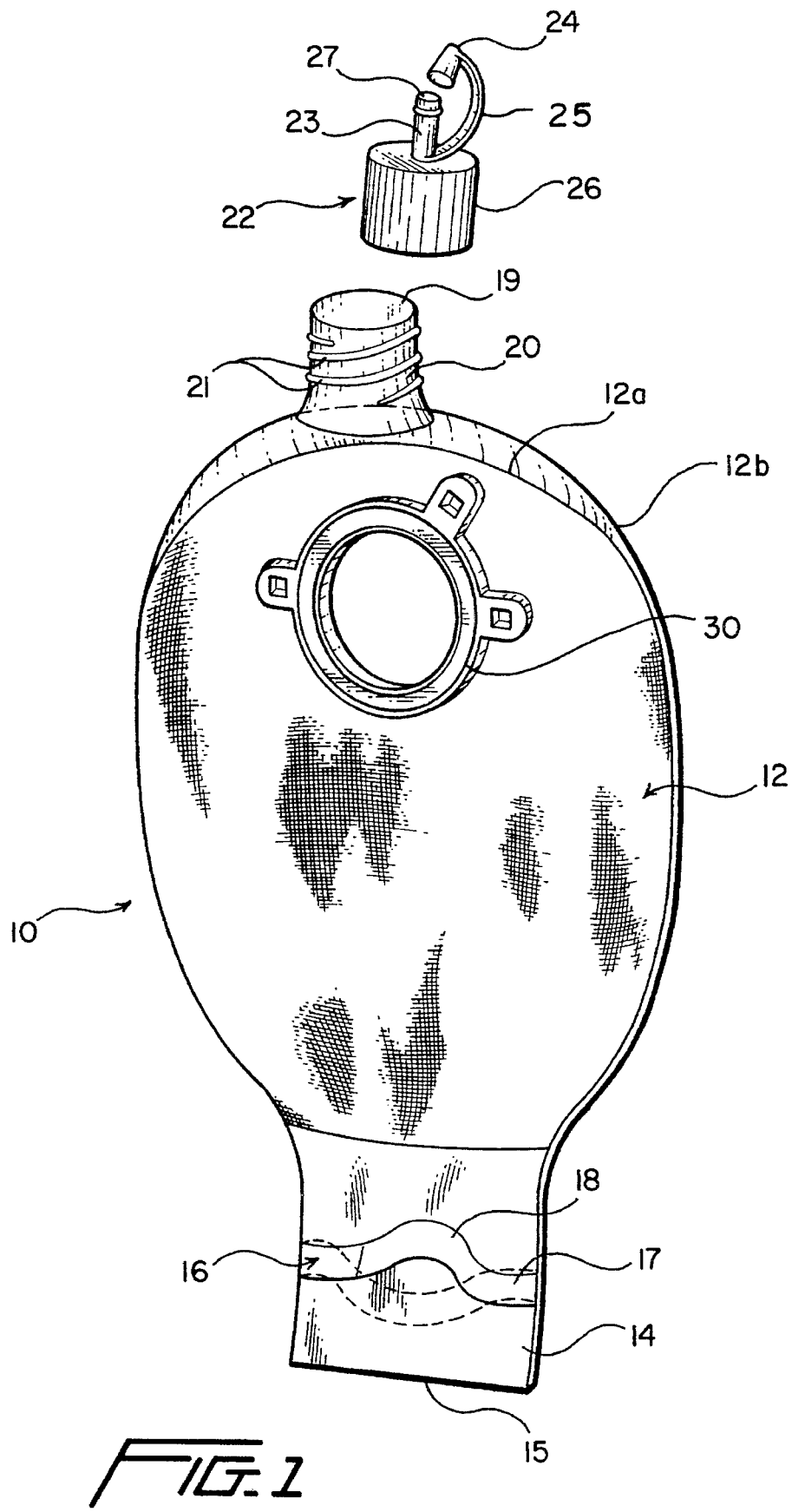
FIG. 1 is a perspective view of the ostomy bag in a first cleaning mode of operation wherein the threaded closure is removed.

The detailed embodiments of the present invention are disclosed herein, however, it is to be understood that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Referring to FIG. 1, an ostomy bag 10 having a flexible body 12 which is formed of any suitable inert, flexible material is shown. At one end of the ostomy bag 10 is tailpiece 14. The tailpiece 14 including a discharge opening 15 and a handle 16. The handle 16 is formed from a strip of material, which in the preferred embodiment is resilient and attached to or formed integrally with one side of the tailpiece 14. However, the tailpiece 14 could include a handle, 16' on both sides thereof if desired. The handle 16 is in the form of a loop having its ends 17 secured to the tailpiece 14 and a center loop portion 18 not secured to the tailpiece 14. The handle 16 allows the wearer to grasp the tailpiece 14 and control the direction of the bodily waste being discharged in a manner which prevents him from coming in contact with any of the discharge. Previously, without the addition of this handle 16, an elderly user would struggle trying to grasp one side of the tailpiece 14, as invariably, he would pinch both sides. The handle 16 is located on the tailpiece 14 such that it does not interfere when the end of the tailpiece 14 is folded and closed by a removable clip assembly (not shown).

The body 12 includes a mouth rim means 30 joined to the front wall 12a of the ostomy bag 10. The mouth rim means 30 is attachable to a stoma flange (not shown) secured on a patient. Above the mouth rim means 30 and on the end of the ostomy bag 10 opposite the tailpiece 14, is a cylindrical, hollow extension piece 0 with external threads 21 thereon. The extension piece 20 in the preferred embodiment is located at the seam of the ostomy bag 10 between front and rear walls 12a and 12b.

The extension piece 20 includes an opening which serves as an entry port 19 for cleaning fluids, i.e., a combination of soap and water. Extension piece 20 is sufficiently rigid in order to maintain the upper portion of walls 12a and 12b spaced apart, thus preventing the walls 12a and 12b of the ostomy bag 10 from collapsing upon each other.

Shown removed from extension piece 20 in FIG. 1 is closure 2. The closure 22, best shown in FIG. 3, includes a cylindrical base portion 26, a vent hose coupling 23 extending outwardly therefrom, an inwardly extending anti-clogging stem 28, a hollow base opening 27 running through both the coupling 23 and stem 28 and a cap 24 secured thereto by a tether 25. Closure 22 is internally threaded so as to cooperate with the external threads 21 on extension piece 20. When cap 24 is secured to vent hose coupling 23 and closure 22 is secured to extension piece 20, both openings 19 and 27 are closed and the ostomy bag 10 is ready for operation in a non-vented mode.

Referring now to FIG. 2, ostomy bag 10 is shown assembled in a venting mode. Instead of vent hose coupling 23 being closed by cap 24, it is open and cooperating with a length of hose 29. Pinch clamp 38 is located along the length of hose 29 in order to control the exhausting of the gases built up within the ostomy bag 10. Again, due to the spacing of the walls 12a and 12b, the location of extension piece 20 above the mouth rim means and the inwardly extending anti-clogging stem 28, the clogging of the vent opening 27 is reduced. Further, because of the anti-clogging stem 28, the vent opening 27 remains unobstructed during use, as any waste traveling upward will collect on the walls of base 26 and not on the end of anti-clogging stem 28.

In operation as a venting assembly, closure 22 is secured to extension piece 20 and vent hose coupling 23 is secured to a length of hose 29, thus, because vent opening 27 is unobstructed, the gases rise out of the ostomy bag 10 and continue out of the hose 29. The pinch clamp 38 is optional, depending upon whether the ostomy bag wearer wants automatic or controlled venting. The purpose of the length of hose is so that venting of the odorous gases do not occur right underneath the wearer's nose.

In operation as a cleaning assembly, while the ostomy bag 10 is in use, the wearer first removes the tailpiece clip 40 to allow the tailpiece 14 to unfold and then grasps handle 16 in order to direct the discharge into a toilet. The closure 22 is then removed and the user may then pour a cleaning solution through opening 19, thus rinsing the ostomy bag 10 from top to bottom due to the location of extension piece 20. If desired, the tailpiece 14 can be folded closed again and clipped, cleaning fluid poured through opening 19, and closure 22 with cap 24 secured on vent hose coupling 23 replaced back on to extension piece 20 to form a closed receptacle. The cleaning fluid within the bag may then be swished around, thereby cleansing the ostomy bag 10 and the stoma. Once cleansing is completed, the handle 16 is grasped, the clip is removed and the unfolded tailpiece 14 is directed to discharge the contents into the toilet.

While various preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. An ostomy bag having a tailpiece which terminates in a discharge opening at one end of the bag, a combination venting/cleaning assembly located at a second end of the bag and a mouth rim means located between the ends of the bag, wherein said venting/cleaning assembly comprises:

a hollow extension piece with a bore therethrough, said extension piece extending outward of the bag at a location above the mouth rim means;

a closure removably attached to the extension piece, including a hollow vent hose coupling with a bore therethrough, said vent hose coupling extending outwardly from the upper surface of said closure; and, wherein the diameter of the bore in the extension piece is greater throughout its length than the diameter of the bore in said vent hose coupling, thereby permitting a hose with a first inner diameter to connected with the vent hose coupling during venting, and a hose of a second, larger inner diameter to be connected with the extension piece during cleaning.

2. The invention of claim 1 further including a length of hose with a first inner diameter which is adapted to cooperate with said hose coupling.

3. The invention of claim 2 including a pinch clamp located along the length of said hose.

4. The invention of claim 1, further including a tethered cap which fits onto the end of said hose coupling to prevent the escape of gases or materials from within the bag.

5. The invention of claim 1, wherein said hollow extension piece is threaded and said closure is threaded so as to cooperate therewith.

6. The invention of claim 1 further including a flexible handle secured on one side of said tailpiece.

7. The invention of claim 6 wherein the flexible handle comprises a strip of material having end portions and a center portion wherein the end portions are secured to the tailpiece and the center portion is unattached and in the form of a loop.

8. The invention of claim 7 wherein the strip of material is formed from a resilient material.

9. The invention of claim 6, further including a flexible handle secured on the other side of said tailpiece.

10. The invention of claim 1, wherein said closure further including an inwardly extending anti-clogging stem opposite said vent hose coupling is which spaced from said hollow extension piece.

11. An ostomy bag having a body portion which extends down into a tailpiece portion with a discharge opening which is closed by folding the tailpiece over upon itself, said ostomy bag comprising:

a mouth rim means located on said body portion;

a handle permanently attached to said tailpiece portion approximate but spaced from said discharge opening; and, said handle being formed from a strip which is located on said tailpiece so as not to interfere with the closing of the tailpiece and including a looped portion.

12. The invention of claim 11 wherein the handle is integrally formed with the ostomy bag.

13. The invention of claim 11 wherein the handle comprises a strip of material having end portions and a center portion wherein the end portions are secured to the tailpiece and the center portion is unattached.

14. The invention of claim 13 wherein the strip of material is formed from a resilient material.

15. The invention of claim 11, further including a flexible handle on each side of said tailpiece.

16. The invention of claim 11 further including a venting/cleaning assembly comprising:

a hollow extension piece having a first portion which is connected to the bag at a location above the mouth rim means and a second portion which extends outside of said bag;

a closure which removably attaches to the second extension portion, including an aperture therein; and a vent hose coupling with a bore therein which cooperates with said aperture in said closure and extends outwardly therefrom.

17. The invention of claim 16, further including an inwardly extending anti-clogging stem which cooperates with said aperture in said closure.

* * * * *